United States Patent
Chavan et al.

(10) Patent No.: US 6,504,044 B2
(45) Date of Patent: Jan. 7, 2003

(54) PROCESS FOR THE PREPARATION OF 1-[CYANO(ARYL)METHYL] CYCLOHEXANOL

(75) Inventors: Subhash Prataprao Chavan, Maharashtra (IN); Subhash Krishnaji Kamat, Maharashtra (IN); Latha Sivadasan, Maharashtra (IN); Kamalam Balakrishnan, Maharashtra (IN); Dushant Anandrao Khobragade, Maharashtra (IN); Ravindranathan Thottapillil, Maharashtra (IN); Mukund Keshao Gurjar, Maharashtra (IN); Uttam Ramrao Kalkote, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/796,084

(22) Filed: Feb. 28, 2001

(65) Prior Publication Data

US 2002/0120164 A1 Aug. 29, 2002

(51) Int. Cl.$^7$ ............................................. C07C 255/00
(52) U.S. Cl. ....................................................... 558/371
(58) Field of Search ........................................ 558/371

(56) References Cited

U.S. PATENT DOCUMENTS

4,535,186 A * 8/1985 Husbands et al. .......... 558/371
5,043,466 A * 8/1991 Shepard ..................... 558/371

FOREIGN PATENT DOCUMENTS

| FR | 1 382 753 A | 8/1950 |
| GB | 2 227 743 A | 8/1990 |
| WO | WO 97/20810 | 6/1997 |

OTHER PUBLICATIONS

Chemical Abstract 133:17266, 1999, Cheng, G & Zhuo, C, XP002168521.

* cited by examiner

Primary Examiner—Alan Siegel
(74) Attorney, Agent, or Firm—Darby & Darby

(57) ABSTRACT

A process for the preparation of 1-[(cyano) aryl methyl] cyclohexanol of the general formula 1 (1a–d) by reacting cyclohexanone with the carbanions of an aryl acetonitrile of the general formula 3 (3a–d),

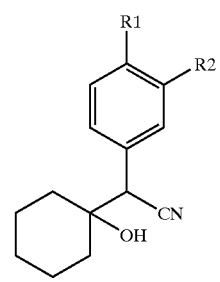
1 a-d

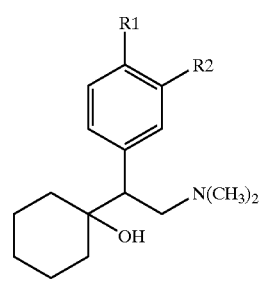
2 a-d

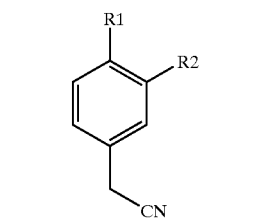
3 a-d a) R1=H, R2=H
b) R1=OMe R2=H
c) R1=OMe R2=OMe
d) R1=OMe R2=cyclopentyloxy using a base, isolating the compound of formula 1 and purifying the compound of formula 1a–d by crystallisation is disclosed.

9 Claims, No Drawings

PROCESS FOR THE PREPARATION OF 1-[CYANO(ARYL)METHYL] CYCLOHEXANOL

FIELD OF THE INVENTION

The present invention relates to a process for the preparation of 1-[(cyano)arylmethyl] cyclohexanol of the general formula 1 from arylacetonitriles of the general formula 3. More particularly the present invention relates to the preparation of 1-[cyano (4-methoxyphenyl) methyl] cyclohexanol of the formula 1b wherein R1=OMe, $R_2$=H which is a key intermediate for the preparation of Venlafaxine of the general formula 2b wherein R1=OMe and R2=H and salts thereof which are well known antidepressants of the central nervous system.

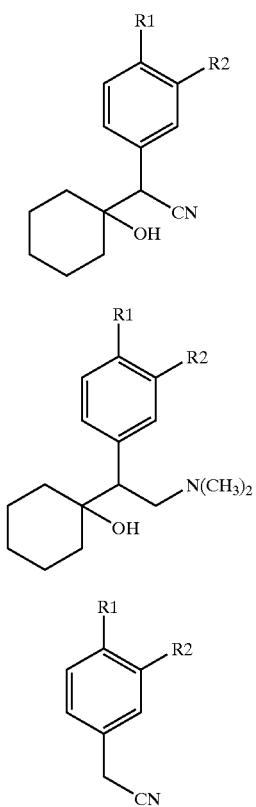

a) R1=H, R2=H
b) R1=OMe R2=H
c) R1=OMe R2=OMe
d) R1=OMe R2=cyclopentyloxy

BACKGROUND OF THE INVENTION

In the prior art [Husbands et al. U.S. Pat. No. 4,535,186 (1985) and EP 0112669B] various 2-aryl-(1-hydroxycyclohexyl)-acetonitriles having formula (1) were prepared with <50% yield by the condensation of arylacetonitriles having formula (3) with cyclohexanone using n-butyl lithium as the base at −70° C. [Sauvetre et al. Tetrahedron 34 2135 (1978)].

UK Patent No GB 2 227 743 A (1990) of Peter Gerald Shepherd discloses the condensation of compounds having formula 3 with cyclohexanone using lithium diisopropylamide in hydrocarbon solvents like hexane, toluene or cyclohexane at ambient temperature thereby improving the yield to 79%.

The use of butyllithium causes great inconvenience in large-scale preparation since butyllithium is very hazardous. The need for setting up plants for operating at very low temperatures combined with the high cost of butyllithium make this method unacceptable for industrial preparations.

OBJECTS OF THE INVENTION

The main object of the present invention is to provide a simple and convenient method of preparation of compounds having formula 1(a–d).

It is another object of the invention to provide a process that avoids the use of expensive and hazardous reagents like n-butyl lithium, lithiumdiisopropylamide.

It is still another object of the invention to provide a process that avoids the use of dry solvents like THF and diethyl ether that are expensive and hazardous.

It is yet another objective of the invention to provide a process that does not require elaborate work up or purification processes like chromatography for the isolation of products.

It is a further object of the invention to provide a process by which near quantitative yields of the product are obtained.

It is another object of the invention to provide a process which is simple, easy to handle, inexpensive and non-hazardous so that large-scale production is possible.

SUMMARY OF THE INVENTION

Accordingly, the present invention relates to a process for the preparation of 1-(cyano)arylmethyl] cyclohexanol of the general formula 1(1a–d), said process comprising reacting cyclohexanone with the carbanions of an aryl acetonitrile of the general formula 3 (3a–d),

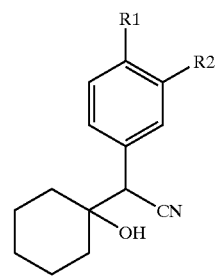

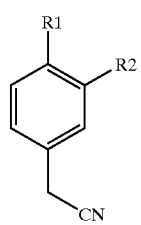

a) R1=H, R2=H
b) R1=OMe R2=H
c) R1=OMe R2=OMe
d) R1=OMe R2=cyclopentyloxy using a base, at temperature in the range of 0–15° for a time period in the range of 15 minutes to 120 minutes, isolating the compound of formula 1 and purifying the compound of formula 1(1a–d) by crystallisation.

In one embodiment of the invention the base used is selected form the group consisting of powdered sodium hydroxide, powdered potassium hydroxide, 10% aqueous sodium hydroxide solution, 10% aqueous potassium hydroxide solution and 50% sodium hydroxide solution.

In another embodiment of the invention the quantity of base used is in the range of 0.25 mole to 1 mole.

In a further embodiment of the invention the quantity of base used is 0.5 mole.

In another embodiment of the invention, the reaction is carried out in the presence of or absence of a phase transfer catalyst.

In another embodiment of the present invention, the phase transfer catalyst used is selected from the group consisting of tetrabutylammonium hydrogensulphate, tetrabutylammonium bromide, tetrabutylammonium chloride, and tetrabutylammonium iodide or benzyltriethyl ammonium chloride.

In still another embodiment of the present invention, the aryl acetonitrile of formula 3 used is selected from the group consisting of phenylacetonitrile, 4-methoxyphenylacetonitrile, 3,4-dimethoxy phenylacetonitrile or 3-cyclopentyloxy, 4-methoxy phenylacetonitrile.

DETAILED DESCRIPTION OF THE INVENTION

The process of the present invention is described by the following examples, which are illustrative only and should not be construed as limit to the scope of the reaction in any manner.

EXAMPLE 1

Phenylacetonitrile 3a (11.7 parts, 0.1 moles) was placed in a beaker and cooled to 0° C. Powdered potassium hydroxide (0.28 parts, 0.05 moles catalytic quantity) and tetrabutylammonium iodide (0.37 parts, 0.01 moles) was added and mixed thoroughly. After 5 minutes, cyclohexanone (9.8 parts, 0.1 moles) was added slowly at 0° C. The mixture on stirring vigorously for 15 minutes solidified suddenly. Water (100 parts) was added at this stage and the reaction mixture stirred for an hour to complete the reaction. The product-1-cyano [(aryl) methyl] cyclohexanol 1a was filtered by suction, washed with water (3×100 parts) and dried to constant weight. 18.7 parts, (87%). Crystallized from ethyl acetate pet ether to yield shining white crystals Mp. 101–2° C. NMR (200 MHz., $CDCl_3$) δ 7.4(s, 5H, aromatic); 3.80 (s, 1H CH CN); 1.59 (m, 10H cyclohexyl); 1.24 (br s, 1H). M+215

EXAMPLE 2

4-Methoxyphenylacetonitrile 3b (147 parts, 1 mole) was cooled to 0° C., and stirred vigorously with a solution of 10% aqueous sodium hydroxide solution (100 parts, 0.25 mol). Tetrabutyl ammonium hydrogen sulphate (4.0 parts, 0.1 mol) was added in one lot while stirring. The reaction was warmed to 15° C. after which, cyclohexanone (100 parts 1.02 mol) was added rapidly in 10 minutes taking care to keep the temperature of the reaction below 15° C. A thick smooth solid separates. At this stage the solid was crushed to fine pieces and water (1000 parts) was added to facilitate stirring. Stirring was continued for 2 hrs. When the reaction was over, (monitored by tlc) the solid was filtered, washed free of alkali and dried to constant weight. Yield 162 parts (97.6%). The product 1-cyano [(4-methoxyphenyl) methyl]-cyclohexanol 1b was crystallized from ethylacetate pet.ether to obtain shining white needles of >99% purity on HPLC M.p 125–6° C. (litt. mp 123–5°). NMR ($CDCl_3$) δ 7.32, 6.95 (4H, q, p-substituted aromatic), 3.8 (3H, s-$OCH_3$); 3.76 (1H, s, CH CN 1.56 (10H, m, aliphatic cyclohexyl); M+245

EXAMPLE 3

3,4-Dimethoxyphenylactonitrile 3c (0.885 parts, 0.005 moles) was cooled to 15° C. in a beaker and stirred vigorously with powdered sodium hydroxide (0.100 parts 0.25 mol). Trimethylbenzylammonium chloride (0.028 parts, 0.003 moles) was added to this mixture followed by cyclohexanone (0.5 parts, 0.005 moles). Stirring was continued for 2 hrs and the reaction was left overnight at 0° C. Water (5 ml) was added after which the solid that separated was filtered, washed with water and dried 0.976 parts (71%). The product 1-cyano [(3,4-dimrthoxyphenyl) methyl] acetonitrile 1c was crystallised from ethylacetate to fine needles. Mp.134–5° C. NMR: ($CDCl_3$) δ 6.85 (m, 3H, aromatic). 3.87(s, 3H O $CH_3$); 3.86(s, 3H O $CH_3$); 3.69(s, 1H, CH CN); 1.59 (m, 10H, cyclohexyl) 1.24 (bs, 1H, OH); M+275

EXAMPLE 4

3-cyclopentyloxy, 4-methoxy phenylacetonitrile 3d (0.3 parts, 0.00129 mols) was cooled to 0° C. and stirred with a 50% solution of sodium hydroxide (0.1 part, 0.00125 moles) and tetrabutylammoniumhydrogensulphate (0.044 parts, 0.000129 mol). Cyclohexanone (0.129 parts 0.0013 moles) was added after 10 minutes and stirring continued for 2 hours to ensure completion of the reaction. The product 1-cyano-[(3-cyclopentyloxy, 4methoxyphenyl) methyl] cyclohexanol 1d was isolated by filtration, washing and drying as a low melting solid. NMR ($CDCl_3$) δ (6.8 (m, 3H, aromatic); 4.75 (br. S, 1H, O—CH—); 3.6 (s 3H, OMe); 3.59 (s, 1H CH—CN); 1.5–2 (m, 18H cyclopentyl and cyclohexyl). M+329

EXAMPLE 5

4-Methoxyphenylacetonitrile 1b (1.47 parts, 0.1 mol) was cooled to 0° C. and stirred with powdered sodium hydroxide (0.02 parts 0.05 mol). Tetrabutylammoniumiodide (0.036 parts 0.01 mol) was added to this mixture and condensed with cyclohexanone (0.98 parts, 0.1 mol) as described above. The product 1b was isolated by filtration, washing and drying of the solid obtained after stirring the reaction mixture for 10 minutes. (2.2 parts, 89.7%)

EXAMPLE 6

4-Methoxyphenylacetonitrile 1b (1.47 parts, 0.1 mol) was cooled to 0° C. and stirred with powdered sodium hydroxide (0.100 parts.0.025 mol) without any phase transfer catalyst. When the reaction became thick, cyclohexanone (0.98 parts, 0.1 mol) was added and the reaction stirred for another 10 minutes till solid separated. The product 1b was isolated as described above. (1.91 part, 78%)

The advantages of the present invention are as follows:

The present invention avoids the use of expensive and hazardous reagents like n-butyl lithium, lithiumdiisopropylamide.

The present invention also avoids the use of dry solvents like THF and diethyl ether, which are also expensive and hazardous. The present method can be conducted in water or even under solvent free conditions.

The present invention does not involve elaborate work up or purification processes like chromatography for the isolation of products.

The present invention avoids the inconvenience of carrying out reactions at very low temperatures.

The present invention does not require the use of inert atmosphere.

The present invention describes a process by which near quantitative yields of the product are obtained.

The present invention describes a process, which is simple, easy to handle, and non-hazardous so that large-scale production is possible.

The present invention presents a very convenient method of preparation of 1 through a simple short and cost effective process.

We claim:

1. A process for the preparation of 1-[(cyano) aryl methyl] cyclohexanol of the general formula 1 (1a–d), by reacting cyclohexanone with the carbanions of an aryl acetonitrile of the general formula 3 (3a–d),

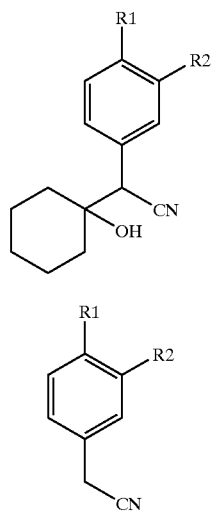

a) R1=H, R2=H
b) R1=OMe R2=H
c) R1=OMe R2=OMe
d) R1=OMe R2=cyclopenyloxy using a base selected from the group consisting of sodium hydroxide and potassium hydroxide at a temperature in the range of 0–15° for a time period in the range of 15 minutes to 120 minutes, isolating the compound of formula 1 and purifying the compound of formula 1a–d by crystallisation.

2. A process as claimed in claim 1 wherein the base used is in an amount in the range of 0.25 mole to 1 mole.

3. A process as claimed in claim 2 wherein the quantity of base used is 0.5 mole.

4. A process as claimed in claim 1 wherein the reaction is carried out in the presence of or absence of a phase transfer catalyst.

5. A process as claimed in claim 4 wherein the phase transfer catalyst used is selected from the group consisting of tetrabutylammonium hydrogensulphate, tetrabutylammonium bromide, tetrabutylammonium chloride, tetrabutylammonium iodide and benzyltriethyl ammonium chloride.

6. A process as claimed in claim 1 wherein the aryl acetonitrile of formula 3 used is selected from the group consisting of phenylacetonitrile 4-methoxyphenylacetonitrile, 3,4-dimethoxy phenylacetonitrile and 3-cyclopentyloxy, 4-methoxy phenylacetonitrile.

7. A process as claimed in claim 1 wherein the reaction is carried out in the presence of a solvent.

8. A process as claimed in claim 7 wherein the solvent used is water.

9. A process as claimed in claim 1 wherein the solvent used is water.

* * * * *